United States Patent
Roemen

(10) Patent No.: US 9,224,056 B2
(45) Date of Patent: Dec. 29, 2015

(54) SYSTEM FOR LOGGING BIOMETRIC DATA

(76) Inventor: Mary K. Roemen, Humble, TX (US)

( * ) Notice: Subject to any disclaimer, the term of this patent is extended or adjusted under 35 U.S.C. 154(b) by 667 days.

(21) Appl. No.: 12/706,045

(22) Filed: Feb. 16, 2010

(65) Prior Publication Data

US 2011/0200236 A1   Aug. 18, 2011

(51) Int. Cl.
*A61B 5/117*   (2006.01)
*G06K 9/00*   (2006.01)
*A61B 5/00*   (2006.01)

(52) U.S. Cl.
CPC .......... *G06K 9/00885* (2013.01); *A61B 5/1172* (2013.01); *A61B 5/1174* (2013.01); *A61B 5/7495* (2013.01)

(58) Field of Classification Search
CPC ....... A61B 5/1174; A61B 5/117; G06T 15/04
USPC .......................................... 382/115, 124, 103
See application file for complete search history.

(56) References Cited

U.S. PATENT DOCUMENTS

| | | | | |
|---|---|---|---|---|
| 2,723,476 A | * | 11/1955 | Lyon ........................... | 15/104.92 |
| 5,071,168 A | * | 12/1991 | Shamos ........................ | 283/117 |
| 5,193,855 A | * | 3/1993 | Shamos ........................ | 283/117 |
| 5,986,746 A | * | 11/1999 | Metz et al. ................... | 356/71 |
| 7,403,644 B2 | * | 7/2008 | Bohn et al. ................... | 382/126 |
| 7,543,156 B2 | * | 6/2009 | Campisi ........................ | 713/186 |
| 8,074,880 B2 | * | 12/2011 | Brown et al. ................. | 235/382 |
| 2005/0099619 A1 | * | 5/2005 | McClurg et al. ............. | 356/71 |
| 2005/0104363 A1 | * | 5/2005 | Wright et al. ................. | 283/68 |
| 2008/0090490 A1 | * | 4/2008 | Barrows et al. .............. | 446/369 |

OTHER PUBLICATIONS

Rizk et al., Prevention of Infant Abductions and Mix-ups in Hospitals Proper Measures for Infant Identification and Security [on-line], Oct. 2009 [retrieved on Dec. 27, 2013], Syndicate of Hospitals in Lebanon, pp. 24-28. Retrieved from the Internet: http://www.syndicateofhospitals.org.lb/magazine/oct09.asp.*

* cited by examiner

*Primary Examiner* — Matthew Bella
*Assistant Examiner* — Dennis Rosario
(74) *Attorney, Agent, or Firm* — Michael L. Greenberg, Esq.; Greenberg & Lieberman, LLC

(57) ABSTRACT

A system for gathering and storing biometric data relating to a portable biometric device that is configured to scan and save the footprint image of an infant, while also automatically compartmentalizing the footprint image into a designated file that also includes an employee identification information of the footprint taker, biometric data of the parent, and both infant and mother wristband identification information. The data and images are collected at the same time, and then time and date stamped, to ensure that no mistakes are made.

3 Claims, 3 Drawing Sheets

SYSTEM FOR LOGGING BIOMETRIC DATA

FIELD OF THE PRESENT INVENTION

The present invention relates to a portable biometric device that is configured to scan the footprints of an infant, while also matching and storing the infant footprints with hospital staff data as well as fingerprints of the infant's mother such that the biometric data can be disseminated, logged and used for appropriate purposes.

BACKGROUND OF THE PRESENT INVENTION

There is a significant rift between proponents of recording newborn infant footprints and those who believe this process is antiquated and ineffective. Typically, hospital and medical employees use an ink and paper method of obtaining such footprints. These footprint images then appear on such identification records as birth certificates. However, the problem as opponents of taking such footprints see it, is that the footprints often are not completely legible. Along those lines, it is contended that infant footprints conducted under current methodology do not provide the level of detail that current digital fingerprinting devices employ.

Even proponents of infant foot printing conceded that current techniques are often not adequate for identification purposes. One of the fundamental reasons for obtaining footprints of newborns is to avoid situations such as abductions and child-switching scenarios—deliberate or accidental. Footprints also are used in many other situations where a small child must be identified. The footprints of a newborn are obtained because medical and law enforcement officials contend that the general process provides a reliable, expeditious, and cost-efficient method for establishing probable personal identity of the child. According to various experts, every child's prints contain friction ridge details that are unique to that person. Even the footprints and fingerprints of identical twins are different, which can cause confusion if the footprint image is confused with other data at the time of its taking. And because the friction ridge detail does not change, law enforcement personnel have been known to identify adult victims of accidents and disasters via the footprints taken as a newborn. Even DNA testing at times has been known to confuse such people as twins, and certainly is more expensive. From this information, the problem is not the value of taking footprints of infants, but rather the quality of such footprints. To this end, the present invention solves this problem by providing a system for obtaining infant footprints in a portable manner that is backed up by safeguards to ensure proper storage and handling.

As mentioned above, the ink and paper technique of obtaining infant footprints is inconsistent and has a less-than-stellar accuracy rate. Medical employees usually are not properly trained in obtaining newborn footprints via inkpad and paper. Oftentimes, such prints are rejected and require the additional cost, time and inconvenience of a redo. In order to fully protect these paper prints, medical employees must scan the paper into a computer. This creates an additional problem of potentially bad or even smudged scans during the transfer process. The present invention solves this need by scanning directly from the infant's foot, as well as other related information that is saved in a compartmentalized file containing only the information of that individual child. This is conducted via the system and process described below where employee identification information is scanned into the file, along with biometric data of the parent, infant and parent wristband identification information, and the infant footprint. This information is collected all at once, then time and date stamped, so that there is no chance for any mistake.

U.S. Pat. No. 7,277,562 issued to Zyzdryn on Oct. 2, 2007 is a biometric imaging capture system and method. Zyzdryn captures print images and determines the quality of such prints. Unlike the present invention, Zyzdryn is not conducive to obtaining footprints of infants as it instead is related to fingerprints. The present invention, in contrast, is a portable system that incorporates a biometric device that is used to obtain and automatically compartmentalize into a designated file the employee identification information of the footprint taker, biometric data of the parent, infant wristband identification information and the infant footprint.

Similar substantial differences relate to U.S. Pat. No. 7,308,122 issued to McClurg et al on Dec. 11, 2007. McClurg is a biometric imaging system and method. McClurg scans fingerprints and then employs an indication system to confirm a good scan. However, McClurg does not offer the additional safeguards of the present invention such as automatically compartmentalizing into a designated file the employee identification information of the footprint taker, biometric data of the parent, infant wristband identification information and the infant footprint. In addition, McClurg is not conducive to infant footprints.

U.S. Pat. No. 6,187,540 issued to Staub et al on Feb. 13, 2001 is a method of newborn identification and tracking. Staub uses genotyping to maintain samples of the newborn and the mother. Unlike the present invention, Staub focuses on these cellular samples, which can be more costly and invasive. In contrast, the present invention is a portable system that incorporates a biometric device that is used to obtain and automatically compartmentalize into a designated file the employee identification information of the footprint taker, biometric data of the parent, infant wristband identification information and the infant footprint. Other items such as U.S. Pat. No. 6,485,981 issued to Fernandez on Nov. 26, 2002 rely on some sort of chemical or substance in their obtaining and tracking methods, as opposed to the present invention which is free of chemicals.

Currently, there is nothing that employs a system for obtaining infant footprints that couples this information with additional tracking mechanisms as described in the present invention. As such, the present invention solves a need in a completely accurate manner in terms of both the actual footprint image capture, as well as the additional safeguards as described.

SUMMARY OF THE PRESENT INVENTION

The present invention relates to a system for logging biometric data of an infant and its mother. More specifically, the present invention is configured to digitally collect a detailed footprint of a small child or infant. A portable biometric device of the present invention scans the footprint image and provides a means for the footprint image to be stored via digital means. The footprint image also will be matched with other stored personal data pertaining to the small child or infant.

In addition to the footprint image, the portable biometric device of the present invention also is configured to obtain biometric data of the infant's mother. Additional embodiments include other caregivers such as a father, although the preferred embodiment relates to the biological mother soon after birth of the child. The parental biometric data in the preferred embodiment is a fingerprint. The parental fingerprint will then be digitally stored with the infant footprint.

The present invention also relates to digital coded data pertaining to a hospital or medical employee such as a maternity nurse. The first step in the process of the present invention is that the medical employee will enter or scan his or her employee identification data into the portable biometric device. The medical employee will then enter or scan into the portable biometric device digital coded data contained in an infant or small child's wristband, as well as coded data contained on the mother's wristband or identification. The medical employee will then collect the footprint image via the portable biometric device, followed by the mother or parent's fingerprint image. The portable biometric device then matches all of the identifications and collected data to ensure proper tracking. It is important that all of the data and images are collected at once, and then time and date stamped, to ensure that there is no chance for mistake.

DETAILED DESCRIPTION OF THE PREFERRED EMBODIMENT

The present invention is a system for collecting, logging and tracking biometric data. The preferred embodiment relates to gathering and maintaining a digital image of a small child or infant's footprint. Safeguards relating to segregating the footprint image with identifiable information assist in the tracking and organizational avenues of the present invention to protect against errors.

Figure 1:
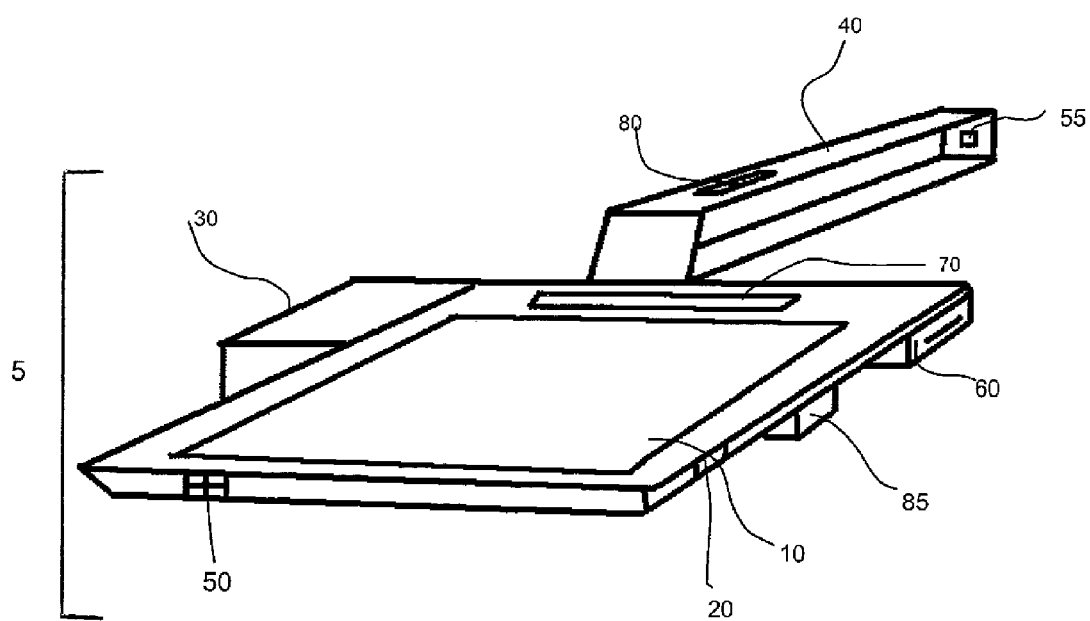
FIG. 1 is a view of an embodiment of the portable biometric device of the present invention.

An embodiment of a portable biometric device (5) of the present invention is seen in FIG. 1. The portable biometric device (5) is configured to accurately collect digital footprint images of a small child or infant. As we see in FIG. 1, a scanning surface (10) is of such length and width to permit a person to help place an infant's foot onto the scanning surface (10). The scanning surface (10) may be either on the top of the portable biometric device (5) or located within an enclosure such that the foot is placed inside an opening of the portable biometric device (5). Both embodiments are such that once the bottom of the foot is flatly pressed against the scanning surface (10), the digital image of the footprint can be collected. The preferred embodiment is that the scanning surface (10) is located on the top of the portable biometric device (5). The scanning surface (10) is conventional and is envisioned to be operated in a similar manner to a charged coupled device (CCD) or contact image sensor (CIS), although other conventional means are envisioned.

In addition to the space allotted for collecting the footprint image, an additional embodiment has a fingerprint zone (20). The fingerprint zone (20) is a marked area along one portion of the scanning surface (10) that permits a digital fingerprint image to be collected by the portable biometric device (5). The fingerprint zone (20) is wide enough for an adult to place a finger onto that portion of the scanning surface (10). However, in the preferred embodiment, the scanning surface (10) is configured to capture both a footprint and a fingerprint without the need for a dedicated zone.

The present invention also includes a conventional identification scanner (30). The identification scanner (30) operates along the lines of a photodiode or laser scanner mechanism in order to scan and read bar codes and other coded information. The identification scanner is configured to read and record a medical employee barcode that is coded into an identification card, as well as the mother's and infant's coded information contained in their hospital wristbands. The preferred embodiment of the placement of the identification scanner (30) is the side of the portable biometric device (5) opposite the handle (40). An additional embodiment relates to a magnetic stripe card reader for swiping identification cards that use a magnetic strip, while yet another embodiment relates to a keypad to enter the medical employee's identification number or code. The portable biometric device (5) is then configured via conventional means to record, track and compartmentalize the data gleaned from the identification scanner (30) into an internal and time-stamped file contained in the conventional memory storage (60) that is in communication with the portable biometric device (5).

The portable biometric device (5) also is configured to be hand held as we see in FIG. 1. A handle (40) is used in the preferred embodiment such that a person can grasp the handle (40) with one hand. The handle also may latch onto a set object in order to assist a person with maneuvering an infant to obtain biometric data or footprints. In an additional embodiment, the handle (40) will not protrude outward to any great length but instead will be more akin to a c-shaped handle similar to that of a briefcase. In addition, an embodiment is envisioned where the handle (40) is retractable. In this embodiment, the handle (40) will retract into and be configured to be pulled or released outward, via any conventional means, such that the user can gain a solid grasp on the portable biometric device (5).

The portable biometric device (5) in the preferred embodiment includes an on/off switch (80). When the on/off switch (80) is switched off, a conventional circuit is opened and the portable biometric device (5) will not function. When the on/off switch (80) is switched on, the conventional circuit is closed and the portable biometric device (5) will operate so long as there is an adequate power source. A power supply housing (85) in the preferred embodiment includes battery storage capability. The conventional battery power is ideal because of the portable nature of the present invention. However, additional avenues such as plugging a cord into the power supply housing or receiving a sustainable charge via connection with a computer connection (55) such as USB port also is envisioned for the present invention.

Once activated, the portable biometric device (5) operates via conventional means as the various data and images are scanned, transmitted and stored. Again, this storage can be within the memory storage (60) or transmitted directly via conventional wireless means via a wireless transmitter (50) to a designated computing or digital data storage device. Moreover, the portable biometric device (5) uses conventional processing technology to analyze the digital images to ensure that the digital images are properly scanned. An indicator (70) notifies the medical employee whether or not the image was properly scanned.

In the preferred embodiment, a green light will appear on the indicator (70) to alert the medical employee that a proper scan was conducted. A red light may indicate an improper or failed scan. However, the indicator (70) also may be a speaker operating in communication with the conventional components of the portable biometric device (5) to alert the medical employee via audio means. A proper scan relates to a complete digital image of the footprint or fingerprint, as well as scanned identification and wristband information. For example, a footprint image that is scanned in such a manner that one side is lighter than the other may indicate that the foot was not placed completely flat onto the scanning surface (10).

Figure 3:
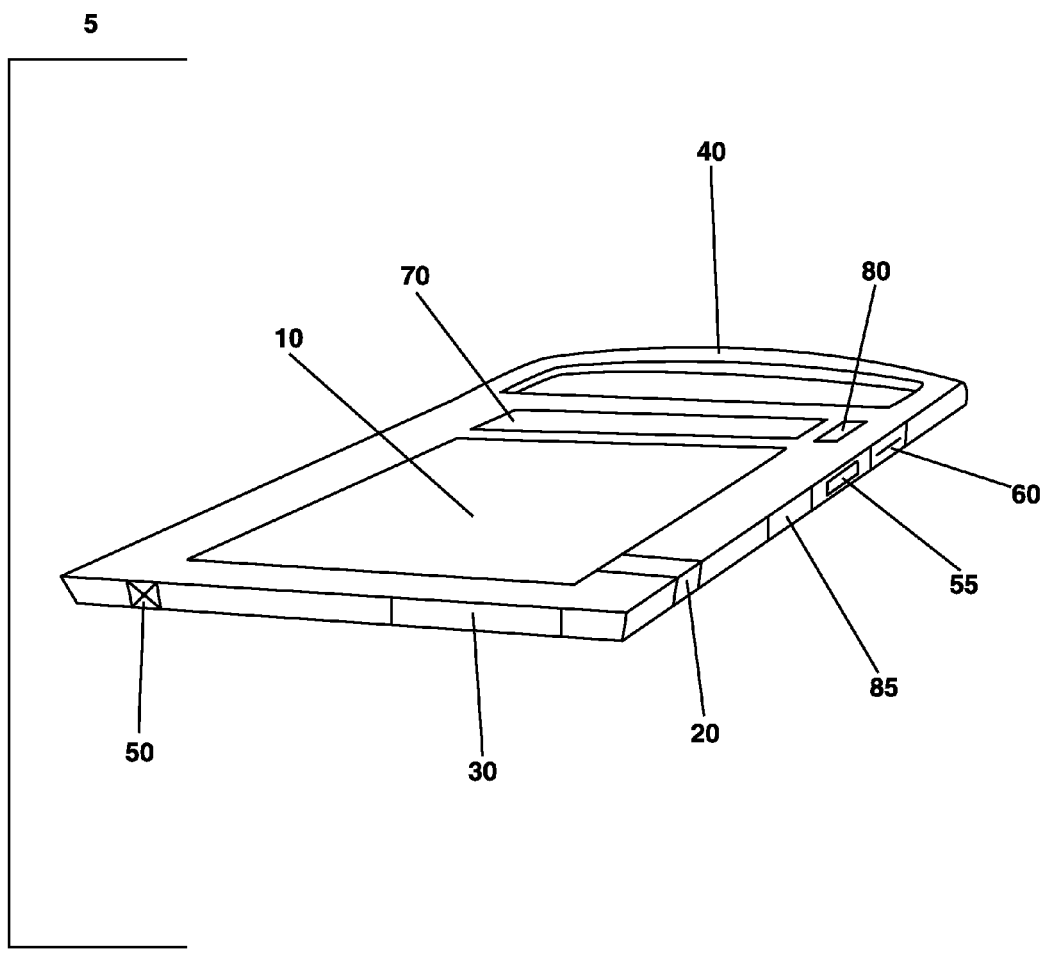
FIG. 3 is an alternative embodiment of the device of the present invention.

An alternative embodiment of the device of the present invention is shown in FIG. 3. The numbers correspond to the same elements of the device of the present invention as described per FIG. 1. Essentially, the alternative embodiment shown in FIG. 3 is more compact than the preceding embodiment. The ID scanner (30) is built into the side of the device opposite the handle rather than extending out to the side of the device. The power supply housing (85) and memory storage (60) are built into the opposite side of the device, instead of extending below it. The handle (40) is a curved c-shape, as opposed to the rectangular protrusion in FIG. 1. The power switch (80) is on the face of the device, and the computer port (55) is built into the side.

Figure 2:
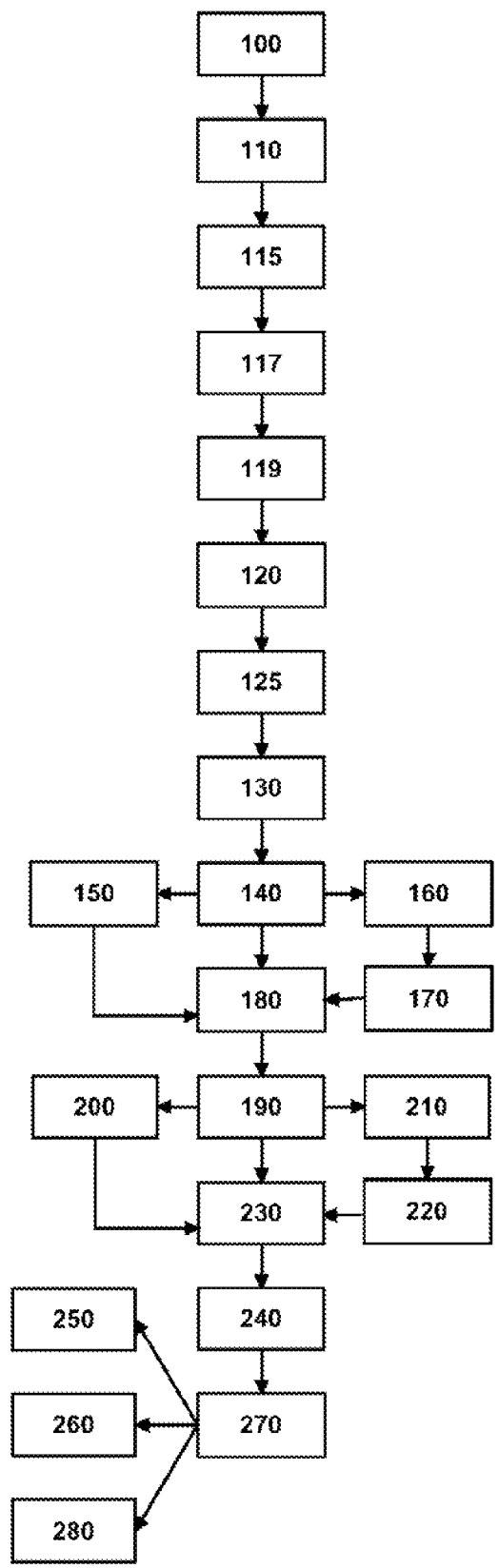
FIG. 2 is a flow chart of the process of the present invention.

FIG. 2 is a flow chart that describes the process of the preferred embodiment of the present invention. The purpose of the present invention is to obtain and store digital biometric data, most notably footprints of infants. In addition, safeguards are employed by the present invention to ensure accuracy of both the scanned images and of the overall file for proper tracking and efficiency.

As we see in FIG. 2, a medical employee will activate (100) the portable biometric device (5) in the manner described above. The medical employee will then enter or scan his or her employee identification data (110) into the portable biometric device (5). This scanning of the employee identification data can be conducted via an identification scanner (30) such as a magnetic swipe card reader or entering an employee ID onto a keypad. The preferred embodiment is such that the identification scanner (30) will be configured to read and store the information contained in the barcode of the employee ID via the laser scanning mechanism or photodiode of the identification scanner (30). However, additional embodiments relate to scanning the employee identification data directly from the scanning surface. Once the employee identification data is scanned, that information is transferred via conventional means to a file (115). This file can be stored in the memory storage (60), which is in communication with the scanning elements of the portable biometric device (5) via conventional means. The file also can be stored in a separate computing device drive via a wireless transmitter (50) or interface that also is in communication with the scanning elements of the portable biometric device (5) via conventional means.

After the employee identification data is scanned, and that information is transferred via conventional means to a file (115), the medical employee will enter or scan into the portable biometric device (5) via the identification scanner (30) the digital coded data contained in the mother's wristband, identification or bracelet (117). Typically, the mother will be fitted with such wristbands or bracelets that contain bar-coded information that identifies the mother and can correlate to the child. Once the wristband or bracelet information data is scanned, the data is transferred via conventional means to the compartmentalized file relating to the infant identification information (119).

The medical employee will then enter or scan into the portable biometric device (5) via the identification scanner (30) the digital coded data contained an infant or small child's wristband or bracelet (120). Typically, infants are fitted with such wristbands or bracelets that contain bar-coded information that identifies the small child. The information contained on the wristband or bracelet is read and scanned into the present invention via similar means as described for the employee identification. Once the wristband or bracelet information data is scanned, the data is transferred via conventional means to the compartmentalized file relating to the infant identification information (125). In fact, the preferred embodiment of the present invention is to incorporate all scanned data pertaining to a particular infant or small child so that all the data is segregated from other files or information (130).

Once the file is created containing the information of the medical employee and infant wristband or bracelet, the medical employee can obtain the footprint of the infant or small child (140). As described above, the bottom of the foot will be pressed firmly onto the scanning surface (10) of the portable biometric device (5) such that the toes, heel and sole can be scanned. The scanning surface (10) in the preferred embodiment is a touch screen scanning area that is about 5" by 4." Dimensions hovering around these numbers permit the portable biometric device (5) to remain portable while also accommodates the sizes of feet of most infants and small children. An additional embodiment of the present invention incorporates conventional optical analysis software combined with the scan to review any abnormal creases or folds that may indicate a complication with one of the many bones found in the infant's foot. In this embodiment, a separate indication alert can call attention to the potential problem.

After the footprint is scanned, the indicator (70) will emit a visual or audio alert relating to the quality of the scan. Operating via conventional means, the present invention reviews the scan to ensure that elements are not missing and/or the scan completely included all parts of the foot. If the scan is deemed acceptable, a positive indication will be emitted from the indicator (70). An example of a positive alert is a green light appearing on the indicator (70). This positive indicator will signal to the technician or medical employee to save the scanned footprint and transmit it into the file (180). Conversely, a scanned footprint that is not deemed acceptable will cause either a negative alert or no alert to be emitted from the indicator (70). This negative alert will signal to the technician or medical employee to re-scan the footprint image (170). Once the re-scan is deemed acceptable, a positive indicator will signal to the technician or medical employee to save the scanned footprint and transmit it into the file (180).

Once the footprint is scanned and saved in the file, the medical employee can obtain a fingerprint of the child's parent or primary caregiver (190). As described above, the finger in the preferred embodiment will be placed in the fingerprint zone (20) and/or scanning surface (10) of the portable biometric device (5). As is the case with the footprint, the present invention will determine the acceptability of the fingerprint scan. If the scan is deemed acceptable, a positive indication will be emitted from the indicator (200). This positive indicator will signal to the technician or medical employee to save the scanned fingerprint and transmit it into the file (230) containing the compartmentalized information pertaining to the infant or small child. Conversely, a scanned fingerprint that is not deemed acceptable will cause either a negative alert or no alert to be emitted from the indicator (70). This negative alert will signal to the technician or medical employee to re-scan the fingerprint image (220).). Once the re-scan is deemed acceptable, a positive indicator will signal to the technician or medical employee to save the scanned fingerprint and transmit it into the file (230).

By scanning and saving the medical employee identification information, mother coded information, infant coded information, footprint image of the infant and fingerprint image of the mother, combining these items into the compartmentalized file ensures that the footprint image is accurately matched with the correct infant data and surrounding personal and care information. The data and images collected are either saved in the memory storage (60) or transmitted wirelessly as described above to a computing device or hard drive. Once all of the required images and data information are collected, saved and scanned by the portable biometric device (5), the file can be transferred to a dedicated record storage system (240). The file, if initially saved or stored in the memory storage (60) of the portable biometric device (5), can be transferred to the record system via conventional means. This includes a USB, SD/MC card or other like transfer device relating to a computer port (55). A wireless transmission also is envisioned for file and data transfer via the conventional wireless transmitter (50) operating in communication with a router system connected to the record system.

Once transferred to a dedicated record storage system (240) and ultimately stored in the dedicated record storage system (270), the parents or caregiver will be able to receive printed paper copies (250) of the footprint image, as well as the option to receive digital copies (260) of the footprint image. The parents or caregiver can then agree to release the digital footprint image and data to various organizations (280) such as police or child safety groups along the lines of the Center for Missing and Exploited Children.

Having illustrated the present invention, it should be understood that various adjustments and versions might be implemented without venturing away from the essence of the present invention. The present invention is not limited to the embodiments described above, and should be interpreted as any and all embodiments within the scope of the following claims.

I claim:

1. A system for logging biometric data, comprising:
a medical employee
providing medical employee identification data into a portable biometric device and
collecting the provided medical employee identification data in a file;
the medical employee
providing child identification data, from a child wristband, into the portable biometric device and
collecting the provided child identification data in the file;
the medical employee
providing mother identification data, from a mother wristband, into the portable biometric device and
collecting the provided mother identification data in the file;
the portable biometric device activated when receiving a foot of a child onto a scanning surface, the scanning surface disposed at a top of the portable biometric device, enabling collection of a child footprint image to the portable biometric device;
the medical employee collecting the child footprint image via the portable biometric device in the file based on the collecting the provided medical employee identification data, the provided child identification data, and the provided mother identification data in the file;
the medical employee collecting a parent fingerprint image via the portable biometric device in the file based on the collecting the child footprint image in the file;
stamping the collected and provided medical employee identification data, the collected and provided child identification data, the collected and provided mother identification data, the collected child footprint image, and the collected parent fingerprint image with a time and date; and
the portable biometric device matching
the collected and provided and stamped medical employee identification data,
the collected and provided and stamped child identification data,
the collected and provided and stamped mother identification data,
the collected and stamped child footprint image, and
the collected and stamped parent fingerprint image with each other for tracking.

2. The system of claim 1, further comprising a parent receiving paper copies of the collected and stamped child footprint image.

3. The system of claim 1, further comprising a parent releasing the collected and stamped medical employee identification data, the collected and stamped child identification data, the collected and stamped mother identification data, the collected and stamped child footprint image, and the collected and stamped parent fingerprint image to safety groups.

* * * * *